United States Patent [19]  [11] 4,156,732
Lang et al.  [45] May 29, 1979

[54] CERTAIN PHARMACEUTICAL SULFAMOYLBENZOYL BENZOFURANS, BENZOTHIOPHENES, AND INDOLES

[75] Inventors: Hans-Jochen Lang, Hofheim am Taunus; Josef Musil, Kirchzarten-Burg; Roman Muschaweck, Frankfurt am Main, all of Fed. Rep. of Germany

[73] Assignee: Hoechst Aktiengesellschaft, Frankfurt am Main, Fed. Rep. of Germany

[21] Appl. No.: 917,194

[22] Filed: Jun. 20, 1978

[30] Foreign Application Priority Data

Jun. 21, 1977 [DE] Fed. Rep. of Germany ....... 2727802

[51] Int. Cl.$^2$ .................. C07D 307/80; A61K 31/40; C07D 209/12

[52] U.S. Cl. .................................... 424/274; 424/275; 424/285; 260/326.12 R; 260/330.5; 260/346.73

[58] Field of Search .................. 260/346.73, 326.12 R, 260/330.5; 424/274, 275, 285

[56] References Cited

U.S. PATENT DOCUMENTS 4,117,151   9/1978   Descamps et al. .............. 260/346.73

*Primary Examiner*—Natalie Trousof
*Assistant Examiner*—Bernard Dentz
*Attorney, Agent, or Firm*—Curtis, Morris & Safford

[57] ABSTRACT

Heterocyclic sulfamoyl-aryl-ketones wherein the heterocyclic component consists of a benzofuran, indole or benzothiophene radical and the sulfamoyl-aryl moiety is ortho-substituted by halogen, methyl or trifluoromethyl having uricosuric, hypouricemic and salidiuretic action and a process for their manufacture.

11 Claims, No Drawings

CERTAIN PHARMACEUTICAL SULFAMOYLBENZOYL BENZOFURANS, BENZOTHIOPHENES, AND INDOLES

Subject of the present invention are compounds of the formula I

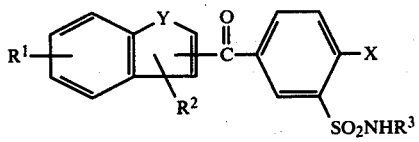  (I)

in which $R^1$ is hydrogen, halogen, alkyl having from 1 to

The 3 carbon atoms, methoxy or ethoxy; $R^2$ and $R^3$, being identical or different, each are hydrogen or alkyl having from 1 to 4 carbon atoms; X is a halogen atom, methyl or trifluoromethyl; solvents Y is oxygen, sulfur or $NR^4$, $R^4$ being hydrogen or alkyl having from 1 to 4 carbon atoms.

Subject of the present invention is furthermore a process for the preparation of compounds of the formula I, which comprises (a) reacting compounds of the formula II

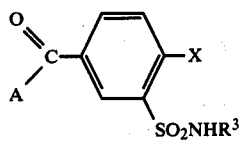  (II)

in which $R^3$ and X are as defined above, and A is halogen, acyloxy, hydroxy or $N(R)_2$, R being hydrogen, lower alkyl or phenyl, with a heterocyclic compound of the formula III

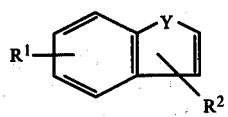  (III)

in which $R^1$, $R^2$ and Y are as defined above, in the presence of a Lewis acid or a protonic acid; or (b) reacting compounds of the formula IV

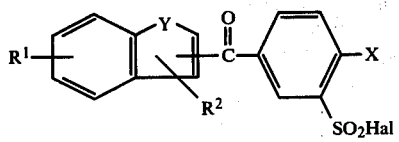  (IV)

with an amine of the formula V $R^3$—$NH_2$ TM (V)

in which formulae $R^1$ to $R^3$, X and Y are as defined above and Hal is halogen; or (c) treating compounds of the formula VI

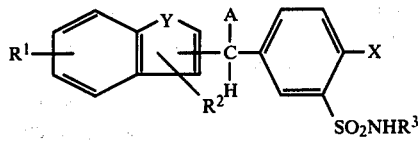  VI in which $R^1$ to $R^3$, A, X and Y are as defined above, with an oxidant; or (d) subjecting compounds of the formula VII

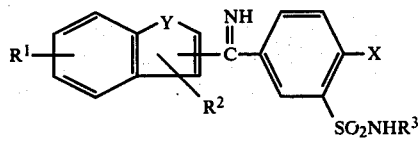  VII in which $R^1$ to $R^3$, X and Y are as defined above, to hydrolysis, optionally in the form of their acid addition salts; or (e) reacting compounds of the formula VIII

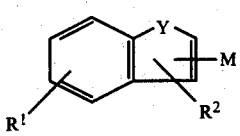  (VIII)

in which $R^1$ and $R^2$ are as defined above, M is Li, MgHal, CdHal, HgHal or $HgOCOCH_3$, and Y is as defined above or NM, with compounds of the formula II, in which A is as defined above or a 2-mercapto-pyridyl radical

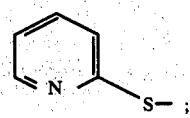

or (f) cyclizing compounds of the formula IX

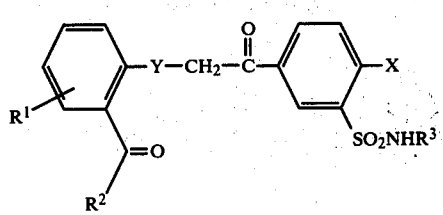  IX and optionally alkylating subsequently the compounds of the formula I, in which $R^3$ is hydrogen obtained according to the operation modes (a) to (f).

The alkyl radicals for $R^1$ to $R^4$ may be linear or branched. The process according to (a) is carried out as follows: the compounds of formula II are reacted with the compounds of formula III preferably in a molar ratio of 1:1; the operation mode, with respect to catalyst, reaction temperature, reaction time, solbents and work-up, being carried out for the rest as indicated in prescriptions for similar examples, e.g. according to Houben-Weyl, Methoden der Organischen Chemie, 4th ed., vol 7/2a, pp. 15–375 (1973).

In the case where A is Hal or acyloxy, halogen-substituted benzene derivatives, for example fluoro-, difluoro-, chloro- or dichlorobenzene have proved to be especially suitable among the solvents used for Friedel-Crafts reactions, alternatively to the usual solvents described in the literature. Preferred Friedel-Crafts catalysts which embrace Lewis-acids as well as protonic acids are aluminum chloride, tin-and titanium-tetrachloride; the use of other catalysts, for example HF, $BF_3$, $ZnCl_2$, $GaCl_3$, $I_2$ being alternatively possible. Preferred protonic acids are HF, $HClO_4$ and polyphosphoric acid. Especially when using aluminum chloride, but also in the case of the other catalysts, it has to be taken into the account that the sulfamoyl function deactivates at least 1 mol of $AlCl_3$ or Lewis acid because of complex formation, so that an excess of at least 2 mols of Lewis acid has to be used.

In the case where A stands for hydroxy, aluminum chloride, zinc chloride, boron trifluoride, or alternatively hydrogen fluoride or perchloric acid, and polyphosphoric acid or phosphorus oxychloride are preferably used as catalysts. On the other hand, $POCl_3$ is advantageously employed as catalytic Lewis acid in the case of reactions of III with the acid amide derivatives of the formula II, in which Y is $-NR_2$.

Operation mode (b) provides reaction in known manner of sulfochlorides of the formula IV with ammonia or an amine, for example according to Houben-Weyl, Methoden der organischen Chemie, 4th ed., vol. 9, (1955) pp. 605–627.

Especially suitable reaction media are polar solvents such as water, lower alcohols having from 1 to 5 carbon atoms, dioxan, tetrahydrofuran, dimethyl acetamide, mono-, di- or triethyleneglycol-dimethyl ether; the reaction being carried out at temperatures of from 0° to 100° C., preferably 10° to 50° C. The reaction time is from ½ to 70 hours, preferably 4 to 14 hours.

The sulfochlorides of the formula IV can be obtained in different ways according to methods known per se. They are preferably prepared by means of the Meerwein reaction (Chem. Ber. 90, 841 (1957)) from the amino derivatives of the formula X

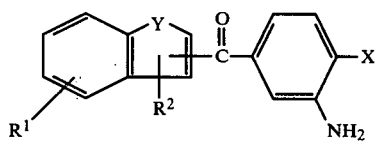

X in which the substituents are as defined above.

The compounds of the formula X are for example obtained from compounds of the formula XI

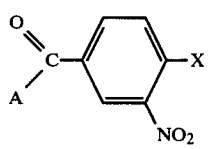

XI in which X and A are as defined above, by a reaction analogous to the operation mode (a) with compounds of formula III and subsequent reduction of the nitro compound XII

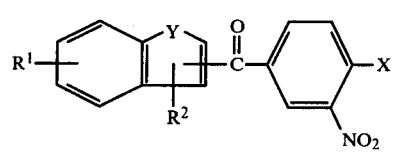

XII

According to operation mode (c), compounds of the formula VI are converted by means of an oxidant to the compounds of formula I. Suitable oxidants are organic and inorganic ones, for example salts and complex compounds of $Fe^{+3}$, nickel peroxide, potassium permanganate, chromium-VI compounds, cooper-II salts, halogen nitrogen oxides such as $N_2O_3$ in situ, or $No_2$, $HNO_3$, oxygen, inorganic or organic peroxo compounds such as $H_2O_2$, benzo-peracid or M-chlorobenzo-peracid, N-chloro-and N-bromo-succinimide, dimethyl sulfoxide, aliphatic nitro compounds or ketones, in the presence of an aluminum alcoholate, according to an Oppenauer oxidation. Reaction and work-up are carried out according to comparable examples described in the literature, for example Houben-Weyl, Methoden d. organischen Chemie, 4th ed., vol. 4/1b (1975), pp. 425, 465, 673, 901, and vol. 7/2a (1973), pp. 677–788. In the case where A is an OH group, a mild and especially suitable oxidant is active manganese-IV oxide (see for example A. J. Fatiadi, Synthesis 1976 65; German Offenlegungsschrift No. 2 436 263), acetonitrile or halogenated hydrocarbons, for example methylene chloride, chloroform, tetrachloroethane, being preferably used and the reaction being carried out at temperatures of from 0° to 40° C., preferably 20° to 30° C., for 6 to 60 hours.

The compounds VI in which A is OH are obtained in usual manner, for example by addition of an aldehyde of the formula XIII

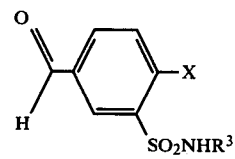

XIII on compounds of the formulae III or VIII.

For the oxidation of compounds VI, in which A is acyloxy, chromic acid is preferably used, see Org. Synth. 42, 79 (1962). In the case where A is halogen, dimethyl sulfoxide, oxides of tertiary amines such as pyridine-N oxide or trimethylamine oxide, or aliphatic nitro compounds such as 2-nitropropane are preferably used alternatively to chromic acid or sodium bichromate. Those compounds VI, in which A is $N(R)_2$, are preferably converted to the compounds I with the use of peroxo compounds or dimethyl sulfoxide; see Org. Prep. Proced. Int. 8 (1976); J. Am Chem. Soc. 97, 5927 (1975).

The compounds VI, in which A is halogen or acyloxy, are obtained for example from the corresponding compounds in which A is OH by acylation or chlorination, and in the case where A is a $N(R)_2$ group, for example from the corresponding compounds in which A is halogen by reaction with amines in usual manner.

According to operation mode (d), ketimines of the formula VII, which may alternatively be present in the form of their acid addition salts, are hydrolyzed. In order to prepare the compounds of formula VII, the nitriles of the formula XIV

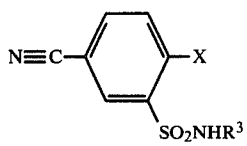

are reacted according to a Houben-Hoesch reaction with compounds of the formula III; see Organic Reactions 5, 387 (1949). The two reactants are reacted preferably in a molar ratio of 1:1 in an anhydrous inert polar organic solvent being for example diethyl ether, di-isopropyl ether, tetrahydrofuran, glacial acetic acid, dioxan, a halobenzene, preferably chlorobenzene, advantageously with the use of mono-, di- or triethyleneglycol-dimethyl or -diethyl ether as solvent. A dry current of HCl gas is introduced into the reaction mixture for 2 to 20 hours, at temperatures of from $-30°$ to $+40°$ C., preferably $-5°$ to $+15°$ C., until saturation is obtained. Subsequently, the mixture is advantageously allowed to stand for 1 to 3 days at $-5°$ to $+15°$ C. Operations may alternatively be carried out in the presence of an additional Lewis acid, especially anhydrous zinc or aluminum chloride.

In order to separate impurities, it is recommended to isolate the ketimine hydrochloride of formula VII obtained as intermediate products, although, in principle, hydrolysis without further isolation and purification operations is possible. The ketimine hydrochlorides are obtained by precipitation with a less polar solvent added, especially diisopropyl ether, ether, or also acetic acid lower alkyl ester, acetone or mixtures of the cited solvents with petroleum ether or cyclohexane.

Hydrolysis of the ketimine hydrochloride can be carried out in alkaline as well as in acidic medium; the compounds VII being heated in water or ethanol/water mixtures, optionally in the presence of a small amount of ammonia, sodium hydroxide solution, calcium carbonate, dilute hydrochloric acid or sulfuric acid, the ketone formed being filtered off or isolated after extraction with an organic solvent, preferably acetic acid ester. The ketimines of formula VII may alternatively be obtained by reaction of compounds of formula VIII with the nitriles of formula XIV according to the method of Blaise; see Houben-Weyl, 4th ed., vol 7/2a, p. 603 (1973).

As solvents there are used the inert and anhydrous solvents usual for organo-metallic reactions, preferably ethers such as diethyl ether, dibutyl ether, and especially tetrahydrofuran or mono-, di- or triethyleneglycol-dimethyl or -diethyl ether. Inert aromatic hydrocarbons such as toluene or xylene or mixtures of the cited solvents may also be employed. In the case where $R^3$ is not hydrogen, at least 2 mols per mol of compound XIV, in the case where $R^3$ is hydrogen, at least 3 moles per mol of XIV have to be used. Operations are carried out preferably at temperatures of from 30° to 130° C. and within 3 to 50 hours. Generally, the reaction mixture is worked up after agitation for 10 to 24 hours by decomposing it with water. The imines so obtained are converted by hydrolysis in an acidic or alkaline medium to the compounds of formula I.

According to operation mode (e), compounds of the formula II are reacted with organo-metallic compounds VIII, using especially the corresponding lithium- und magnesium-organic compounds. In this operation mode, A in the compounds of the formula II may also stand for a mercapto-pyridyl radical; see Bull. Chem. Soc. Japan 47, 1777 (1974).

Per mol of the compounds II, about 2 to 5° mols of compound VIII are used when $R^3$ is not hydrogen, and about 3 to 3.5 mols VIII when $R^3$ is hydrogen. The reaction is carried out in an inert and anhydrous solvent usual for organo-metallic reactions, preferably ether, tetrahydrofuran, dioxan or a mono-, di- or triethyleneglycol-dimethyl or -diethyl ether, and preferably at temperatures of from -100° to +100° C. The reaction being complete, the reaction products are hydrolyzed in known manner, for example by introducing the reaction mixture at temperatures of from $-5°$ to $+20°$ C. and while maintaining a pH range of from 6 to 11 into an aqueous saturated ammonium chloride solution.

The compounds of formula VIII preferably used in operation mode (e), in which M is Li or MgHal, may be obtained by reacting halogen compounds of the formula XIV

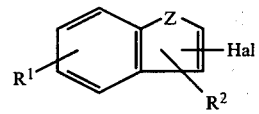

or compounds III with the metal M or, as is especially preferred, organo-metallic compounds R—M in which M is MgHal or Li, according to the method known from Houben-Weyl, 4th ed., vol. XIII/1, (1970), pp. 93–157, and vol. XIII/2a (1973), pp. 54–152.

According to operation mode (f), compounds of the formula IX are cyclized under usual conditions (see for example Advances Het. Chem., vol. 18, p. 338 (1975), or vol. 11, p. 178 (1970)). The cyclo-condensation may be carried out in the presence of acidic or alkaline catalysts, the latter being preferred. Advantageously, alkali metal salts of weak acids are used, for example the salt of a weak organic acid, such as sodium or potassium acetate, in glacial acetic acid as suitable solvent; or sodium or potassium carbonate, sodium or postassium alcoholates such as ethylate or methylate, or metal hydroxides such as NaOH or KOH, in a suitable polar organic solvent such as acetone, methylethylketone, dimethyl formamide, dimethyl acetamide or lower alcohols having from 1 to 4 carbon atoms, or mixtures of the cited solvents. Operations are carried out for ½ to 12 hours at temperatures of from 0° to 140° C., preferably 50° to 100° C. In the subsequent treatment of the reaction product with water, a pH below 9 should be adjusted, in order to prevent salt formation of the sulfamoyl group.

The starting products of formula IX are obtained by reaction of a halogeno-ketone of the formula XV

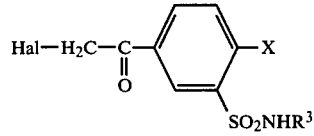

in which Hal is preferably bromine or iodine, with compounds known from the literature and having the formula XVI

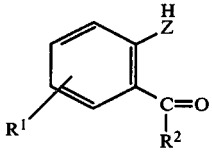

in which Z is preferably S or O. Operations are carried out with the use of bases as described for the cyclo-condensation and of solvents cited there, preferably under gentle temperature conditions in a range of from −10 to +60° C., preferably from 10° to 40° C. Preparation of IX and the cyclo-condensation thereof to form the compounds I may alternatively be carried out without isolating the compounds IX in one step.

The compounds of formula I according to the invention, in which $R^3$ is lower alkyl, can be obtained alternatively by alkylation in known manner of the unsubstituted sulfamoyl group. For this alkylation reaction, usual alkylating agents of the formula $R^3$—X are used, X being for example bromine, iodine, chlorine, —O—SO$_2$CH$_3$, —O—SO$_2$OR$^3$ or

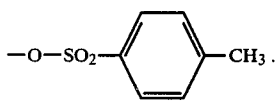

The alkylation can be carried out in water or, preferably, polar organic solvents such as a lower alcohol having from 1 to 4 carbon atoms, dioxan, tetrahydrofuran, dimethyl formamide, dimethyl acetamide or a mono-, di- or triethyleneglycol-mono- or dimethyl or -ethyl ether, at temperatures of from −20° to +50° C., preferably 15 to 35° C., the reaction being allowed to proceed for 5 to 72 hours. As acid-binding bases, there are used for example carbonates, alcoholates or hydroxides of sodium or potassium.

The most important compounds of the invention are those of the formula I, in which the substituent X is bromine or chlorine, preferably chlorine; $R^3$ is hydrogen, methyl or ethyl, preferably hydrogen; $R^2$ is hydrogen, methyl or ethyl; $R^1$ is hydrogen, chlorine, methyl or methoxy in 4- or 5- position of the heterocycle preferably hydrogen; and Y is oxygen or sulfur.

Apart from the substances described in the Examples, the following compounds of the formula I can also be obtained in accordance with this invention:
1. 3-(4-Chloro-3-sulfamoylbenzoyl)-benzo[b]furan
2. 3-(4-Bromo-3-sulfamoylbenzoyl)-benzo[b]furan
3. 3-(4-Chloro-3-methylsulfamoylbenzoyl)-benzo[b]furan
4. 3-(4-Chloro-3-methylsulfamoylbenzoyl)-2-methylbenzo[b]furan
5. 3-(4-Bromo-3-sulfamoylbenzoyl)-2-methylbenzo[b]furan
6. 2-Methyl-3-(3-sulfamoyl-4-trifluoromethylbenzoyl)-benzo[b]furan
7. 2-Ethyl-3-(4-chloro-3-sulfamoylbenzoyl)-5-methoxybenzo[b]furan
8. 2-Ethyl-3-(3-sulfamoyl-4-trifluoromethylbenzoyl)-benzo[b]furan
9. 3-(4-Chloro-3-sulfamoylbenzoyl)-2-propylbenzo[b]furan
10. 3-(4-Chloro-3-sulfamoylbenzoyl)-2-isopropylbenzo[b]furan
11. 2-Butyl-3-(4-chloro-3-sulfamoylbenzoyl)-benzo[b]furan
12. 2-(4-Chloro-3-sulfamoylbenzoyl)-3-methylbenzo[b]furan
13. 2-(4-Bromo-3-sulfamoylbenzoyl)-benzo[b]furan
14. 2-(3-Sulfamoyl-4-trifluoromethylbenzoyl)-benzo[b]furan
15. 3-Ethyl-2-(4-chloro-3-sulfamoylbenzoyl)-benzo[b]furan
16. 2-(4-Chloro-3-methylsulfamoylbenzoyl)-3-methylbenzo[b]thiophene
17. 2-(4-Chloro-3-propylsulfamoylbenzoyl)-3-methylbenzo[b]thiophene
18. 2-(4-Chloro-3-isopropylsulfamoylbenzoyl)-3-methylbenzo[b]thiophene
19. 2-(3-Butylsulfamoyl-4-chlorobenzoyl)-3-methylbenzo[b]thiophene
20. 3-Ethyl-2-(4-chloro-3-sulfamoylbenzoyl)-benzo[b]thiophene
21. 3-Ethyl-2-(4-chloro-3-sulfamoylbenzoyl)-5-methoxybenzo[b]thiophene
22. 3-Methyl-2-(3-sulfamoyl-4-trifluoromethylbenzoyl)-benzo[b]thiophene
23. 3-Ethyl-2-(4-chloro-3-isopropylsulfamoylbenzoyl)-benzo[b]thiophene
24. 3-(4-Chloro-3-sulfamoylbenzoyl)-benzo[b]thiophene
25. 3-(4-Chloro-3-sulfamoylbenzoyl)-2-methylbenzo[b]thiophene
26. 2-Ethyl-3-(4-chloro-3-sulfamoylbenzoyl)-benzo[b]thiophene
27. 3-(4-Chloro-3-sulfamoylbenzoyl)-2-isopropylbenzo[b]thiophene
28. 3-(4-Chloro-3-methylsulfamoylbenzoyl)-2-methylbenzo[b]thiophene
29. 2-Ethyl-3-(4-chloro-3-methylsulfamoylbenzoyl)-benzo[b]thiophene
30. 5-Chloro-3-(4-chloro-3-sulfamoylbenzoyl)-2-methylbenzo[b]thiophene
31. 3-(4-Bromo-3-sulfamoylbenzoyl)-2-methylbenzo[b]thiophene
32. 2-Methyl-3-(3-sulfamoyl-4-trifluoromethylbenzoyl)-benzo[b]thiophene
33. 3-(3-Butylsulfamoyl-4-chlorobenzoyl)-2-methylbenzo[b]thiophene
34. 3-(4-Chloro-3-sulfamoylbenzoyl)-5-methoxy-3-methylbenzo[b]thiophene
35. 2-Ethyl-3-(4-bromo-3-sulfamoylbenzoyl)-benzo[b]thiophene
36. 2-(4-Chloro-3-sulfamoylbenzoyl)-indole
37. 2-(4-Chloro-3-sulfamoylbenzoyl)-3-methylindole
38. 2-(4-Chloro-3-sulfamoylbenzoyl)-1-methylindole
39. 2-(4-Chloro-3-sulfamoylbenzoyl)-1,3-dimethylindole
40. 1-Ethyl-2-(4-chloro-3-sulfamoylbenzoyl)-3-methylindole
41. 3-Ethyl-2-(4-chloro-3-sulfamoylbenzoyl)-1-methylindole
42. 3-Ethyl-2-(4-chloro-3-sulfamoylbenzoyl)-indole
43. 2-(4-Bromo-3-sulfamoylbenzoyl)-1,3-dimethylindole
44. 2-(4-Chloro-3-sulfamoylbenzoyl)-5-methoxy-3-methylindole
45. 5-Ethoxy-2-(4-chloro-3-sulfamoylbenzoyl)-3-methylindole
46. 2-(4-Chloro-3-methylsulfamoylbenzoyl)-1,3-dimethylindole 47. 2-(4-Chloro-3-propylsulfamoylbenzoyl)-1,3-dimethylindole
48. 2-Ethyl-3-(4-chloro-3-sulfamoylbenzoyl)-indole
49. 1-Ethyl-3-(4-chloro-3-sulfamoylbenzoyl)-2-methylindole
50. 3-(4-Bromo-3-sulfamoylbenzoyl)-2-methylindole
51. 3-(4-Bromo-3sulfamoylbenzoyl)-1,2-dimethylindole
52. 3-(4-Chloro-3-sulfamoylbenzoyl)-5-methoxy-2-methylindole
53. 5-Ethoxy-3-(4-chloro-3-sulfamoylbenzoyl)-1,3-dimethylindole
54. 3-(Chloro-3-sulfamoylbenzoyl)-2-methyl-1-propylindole
55. 3-(4-Chloro-3-methylsulfamoylbenzoyl)-2-methylindole
56. 3-(4-Chloro-3-methylsulfamoylbenzoyl)-1,2-dimethylindole
57. 1,2-Dimethyl-3-(3-sulfamoyl-4-trifluoromethylbenzoyl)-indole
58. 5-Ethoxy-3-(4-chloro-3-sulfamoylbenzoyl)-2-methylindole
59. 2-(4-Chloro-3-sulfamoylbenzoyl)-7-methoxybenzo[b]furan
60. 2-(4-Chloro-3-sulfamoylbenzoyl)-5-methoxybenzo[b]furan
61. 2-Ethyl-3-(4-chloro-3-sulfamoylbenzoyl)-5-methoxybenzo[b]furan
62. 2-Ethyl-3-(4-chloro-3-sulfamoylbenzoyl)-7-methoxybenzo[b]furan
63. 2-(4-Chloro-3-sulfamoylbenzoyl)-6-methoxybenzo[b]furan
64. 2-(4-Chloro-3-methylsulfamoylbenzoyl)-6-methoxybenzo[b]furan
65. 2-(4-Chloro-3-sulfamoylbenzoyl)-5-methoxybenzo[b]furan
66. 2-(4-Chloro-3-methylsulfamoylbenzoyl)-5-methoxybenzo[b]furan
67. 2-(4-Chloro-3-sulfamoylbenzoyl)-4-methoxybenzo[b]furan
68. 5-Ethoxy-2-(4-chloro-3-sulfamoylbenzoyl)-benzo[b]furan
69. 6-Ethoxy-2-(4-chloro-3-sulfamoylbenzoyl)-benzo[b]furan
70. 2-Ethyl-3-(4-chloro-3-sulfamoylbenzoyl)-7-methoxybenzo[b]furan
71. 2-Ethyl-3-(4-chloro-3-sulfamoylbenzoyl)-6-methoxybenzo[b]furan
72. 2-Ethyl-5-ethoxy-3-(4-chloro-3-sulfamoylbenzoyl)-benzo[b]furan
73. 2-Ethyl-3-(4-chloro-3-methylsulfamoylbenzoyl)-7-methoxybenzo[b]furan The compounds of the invention are valuable medicaments having a very good action of lowering the uric acid level in the blood of patients, which activity is due to an uricosuric effect.

It is known that most of the medicaments used for treating uricopathic syndromes do not contain a component having a salidiuretic action. In contrast thereto, the compounds of the invention have a good diuretic and saluretic activity, which is wanted, and they are therefore superior to the uricosuric agents hitherto known.

The uricosuric activity of the novel products in accordance with this invention was tested on rats being treated with oxonate at a unit rate of 50 mg/kg per os. In these tests, the compounds of the invention proved to have the same antiuricopathic activity as known commercial products of the probenecide and benzobromaron types.

The salidiuretic activity of the compounds of the invention was tested on rats at a unit rate of 50 mg/kg per os. The compounds showed the same salidiuretic effect as that of known commercial products such as chlorothalidon. Moreover, the novel products are distinguished by a long-duration effect, so that they are also suitable for treating hypertonic syndromes of man. For this purpose, they may be combined with antihypertensive agents.

Suitable therapeutic administration forms of the novel compounds are tablets, dragées, capsules, suppositories and ampoules for parenteral (intravenous, subcutaneous or intramuscular) administration.

The therapeutic unit dose is from 5 to 1000 mg, preferably 10 to 500 mg, per tablet.

Especially for treating hypertension, these formulations may contain an antihypertensive agent in addition to usual fillers and carriers, for example reserpin, hydralazin, guanethidin, α-methyldopa, a β-sympaticolythic agent or clonidine.

Furthermore, therapeutic combination products containing potassium retaining compounds, for example aldosterone antagonists, such as spironolactone, or pseudo-aldosterone antagonists such as triamterene or amiloride, are of interest. Furthermore, $K^+$ substitution may be ensured in different administration formulations, for example dragées, tablets, effervescing tablets, juices etc.

Combinations of the compounds of the invention with another antihyperuricemic agent, which increases the antiuricopathic effects via hindrance of xanthinoxidase, may be of therapeutic interest. An optionally intended increase of the salidiuretic activity can be obtained by combination of the compounds of the invention with a salidiuretic agent.

The following examples illustrate the invention. The indicated melting and decomposition points are not corrected.

EXAMPLE 1

2-Ethyl-3-(4-chloro-3-sulfamoylbenzoyl)-benzo[b]furan 10 mg of powdered 4-chloro-3-sulfamoylbenzoyl chloride (melting point, m.p. 166° C.), prepared from 4-chloro-3-sulfamoylbenzoic acid and thionyl chloride, are introduced into 70 ml of anhydrous chlorobenzene, subsequently 6.32 g of 2-ethylbenzo[b]furan are added, and the reaction mixture is cooled to 0° C. After addition of 11.4 g of anhydrous aluminum chloride, the reaction batch is maintained at a temperature of 5° to 10° C., subsequently stirred for 5 hours at 15° C., and the mixture is then poured into a suspension of 200 g of ice and 10 ml of concentrated hydrochloric acid. After extraction with ethyl acetate and washing with water, the organic phase is stirred for 6 hours with a dilute $NaHCO_3$ solution having a pH of 8.5, dried over magnesium sulfate, and, after evaporation, a light yellow to colorless viscous oil is obtained which crystallizes from petroleum ether. Colorless crystals, m.p. 170°–172° C. (from a small amount of methanol).

EXAMPLE 2

2-Ethyl-3-(3-butylsulfamoylbenzoyl)-benzo[b]furan is obtained as described in Example 1 from 10 g of 3-butylsulfamoyl-4-chlorobenzoyl chloride and 5.1 g of 2-ethylbenzo[b]-furan in the presence of 9.4 g of aluminum chloride, in the form of a colorless to slightly yellow viscous oil.

EXAMPLE 3

2-Ethyl-3-(4-chloro-3-sulfamoylbenzoyl)-5-methyl-benzo[b]furan is obtained as described in Example 1 from 10 g 4-chloro-3-sulfamoylbenzoyl chloride and 6.2 g 2-ethyl-5-methylbenzo[b]furan in the presence of 11.4 g aluminum chloride. Colorless crystals, m.p. 147°–150° C. (from methanol).

EXAMPLE 4

2-Ethyl-5-chloro-3-(4-chloro-3-sulfamoylbenzoyl)-benzo[b]furan is obtained as described in Example 1 from 10 g 4-chloro-3-sulfamoylbenzoyl chloride and 7.06 g 2-ethyl-5-chlorobenzo[b]furan in the presence of 11.4 g aluminum chloride. Colorless crystals, m.p. 130°–133° C.

EXAMPLE 5

3-(4-Chloro-3-sulfamoylbenzoyl)-2-methylbenzo[b]furan is obtained as described in Example 1 from 10.1 g 4-chloro-3-sulfamoylbenzoyl chloride and 5.8 g 2-methyl-benzo[b]furan in the presence of 11.4 g aluminum chloride. After evaporation of the extraction agent, the residue is stirred with di-isopropyl ether, and the solids are filtered off. Colorless crystals, m.p. 183° C. (from methanol).

EXAMPLE 6

2-Ethyl-3-(4-chloro-3-methylsulfamoylbenzoyl)-benzo[b]furan is obtained as described in Example 1 from 10.7 g 4-chloro-3-methylsulfamoylbenzoyl chloride and 6.4 g 2-ethylbenzo[b]furan in the form of amorphous solids having a softening point of 63° C.

EXAMPLE 7

2-Ethyl-3-(4-bromo-3-sulfamoylbenzoyl)-benzo[b]furan is obtained as described in Example 1 from 10.9 g 4-bromo-3-sulfamoylbenzoyl chloride and 6 g 2-ethylbenzo[b]furan in the presence of 11.7 g aluminum chloride. Colorless crystals, m.p. 202°–206° C. (ether).

EXAMPLE 8

2-(4-Chloro-3-sulfamoylbenzoyl)-benzo[b]furan (a) 2-(4-Chloro-3-nitrobenzoyl)-benzo[b]furan 16.6 g salicyl aldehyde are rapidly added dropwise under nitrogen gas to a sodium methylate solution prepared from 3.13 g sodium and 170 ml methanol, subsequently the solvent is distilled off, and the residue is suspended in 150 ml anhydrous toluene. 38 g Bromo-4'-chloro-3'-nitro-acetophenone in 100 ml toluene are added to the mixture with agitation, and the whole is refluxed for a further 3 hours. After standing overnight at room temperature, the solvent is distilled off, and the residue is recrystallized from ethanol. Light yellow crystals, m.p. 132° C.

(b) 2-(3-Amino-4-chlorobenzoyl)-benzo[b]furan 37 g 2-(4-Chloro-3-nitrobenzoyl)-benzo[b]furan are refluxed with agitation for 4 hours in a mixture of 500 ml 50% aqueous acetic acid, 250 ml ethanol and 90 g powdered nickel/aluminum alloy (1:1). After filtration of the metal powder, the solvent is distilled off, water is added to the residue, and extraction is carried out with ethyl acetate. After evaporation of the solvent, colorless crystals having a melting point of 137° C. (from isopropanol) are obtained.

(c) 2-(4-Chloro-3-chlorosulfonylbenzoyl)-benzo[b]furan 3 g 2-(3-Amino-4-chlorobenzoyl)-benzo[b]furan are suspended in 10 ml glacial acetic acid and 5 ml water, and subsequently, 10 ml concentrated hydrochloric acid are added. At a temperature of 0° to 5° C., a solution of 1 g sodium nitrite in 4 ml water is introduced dropwise below the surface and with agitation. Subsequently, the reaction mixture is introduced in portions into a mixture of 2.3 g $CuCl_2 \times 2\ H_2O$ in 70 ml $SO_2$-saturated glacial acetic acid solution, and after a 20 minutes agitation, the volume is doubled by adding water. Agitation is continued for a further 45 minutes, the crystals are filtered off and dried. M.p. 131° C. (decomposition).

(d) 2-(4-Chloro-3-sulfamoylbenzoyl)-benzo[b]furan 3.3 g 2-(4-Chloro-3-chlorosulfonylbenzoyl)-benzo[b]furan are introduced into 19 ml 25% aqueous ammonia solution, and after standing overnight, the liquid is distilled off. After addition of water, the pH is adjusted to 6 by means of dilute HCl, agitation is continued for a further 30 minutes, and the product is crystallized from a small amount of glacial acetic acid. Colorless crystals, m.p. 181° C.

EXAMPLE 9

3-(4-Chloro-3-sulfamoylbenzoyl)-benzo[b]thiophene 5.1 g of powdered 4-chloro-3-sulfamoylbenzoyl chloride are introduced into a solution of 3 g benzo[b]thiophene in 50 ml anhydrous toluene, and subsequently, 12 g titanium tetrachloride are added with agitation. Agitation is continued for 15 minutes at room temperature, the mixture is heated to boiling for about 15 minutes, cooled and poured onto a water/ice suspension. Extraction is carried out then with 70 acetic ester, the organic phase is separated and stirred for 5 hours with an aqueous sodium bicarbonate solution having a pH of 8.5. After separation of the organic phase and drying thereof over magnesium sulfate, the solvent is distilled off and the residue crystallized from toluene. M.p. 154°–156° C.

EXAMPLE 10

3-(4-Chloro-3-sulfamoybenzoyl)-2-methylindole (a) 2.5 g 4-Chloro-3-sulfamoylbenzoyl chloride are suspended in 25 ml dichloro-ethane, and added in portions with agitation to a suspension of 2.7 g aluminum chloride in 25 ml dichloro-ethane, while maintaining the temperature in a range of from −10° to 0° C. The clear solution obtained is stirred for 1 hour at 5° C., subsequently heated to 30° C., and a solution of 1.3 g 2-methylindole in 25 ml dichloro-ethane is added, while maintaining the temperature at 30°–40° C. The reaction mixture is cooled to about 10° C., then decomposed with icewater and extracted twice with ethyl acetate. The united organic phases are stirred for 8 hours with aqueous sodium bicarbonate solution having a pH of 8–9, washed with water, dried over sodium sulfate, and the solvent is eliminated under reduced pressure. The residue is stirred with diisopropyl ether, and the crystalline solids are filtrered off. M.p. 258°–260° C.

(b) 3.1 g 4-Chloro-3-sulfamoylbenzoic acid-N,N-dimethylamide, prepared from 4-chloro-3-sulfamoylbenzoyl chloride and aqueous dimethylamine solution (m.p. 143° C.), are heated to 80° C. for 2 hours with agitation and exclusion of atmospheric humidity together with 0.8 g 2-methylindole and 0.7 ml phosphorus oxychloride. The pH is adjusted in the alkaline range by means of 2 N NaOH, the batch is stirred at room temperature for 40 hours, the pH is then adjusted to 7–8, and the crystals are filtered off. M.p. 257°–260° C.

(c) A hydrogen chloride gas current is introduced for 5 hours at 15°–20° C. into a solution of 10 g 4-chloro-3-sulfamoylbenzonitrile, prepared by refluxing 4-chloro-3-sulfamoylbenzamide in phosphorus oxychloride (m.p. 199° C.), and 6.06 g 2-methylindole in 80 ml anhydrous diethyleneglycoldimethyl ether, and the mixture is then abandoned for 72 hours at 10°–15° C. By pouring the reaction mixture into ethyl acetate, the 4-chloro-3-sulfamoylphenyl-2-methyl-3-indolyl-ketonimine hydrochloride precipitates in the form of crystals. M.p. 320° C.

9 g ketonimine hydrochloride are dissolved in hot water, hydrolyzed after addition of aqueous ammonia with agitation at 50°–60° C., and the crystalline 3-(4-chloro-3-sulfamoybenzoyl)-2-methylindole is filtered off. M.p. 252°–257° C.

(d) A solution of 17 g 2-methylindole in 200 ml tetrahydrofuran is rapidly added to a solution of methylmagnesium iodide, prepared from 3.28 g magnesium chips in 80 ml anhydrous ether and 22.5 g methyl iodide, and the batch is refluxed for about 15 minutes. Subsequently, a solution of 15.75 g 4-chloro-3-sulfamoylbenzoyl chloride in 100 ml tetrahydrofuran is rapidly added by pouring, refluxing is continued for a further 14 hours, the batch is cooled and poured into a solution of 20 g ammonium chloride in 200 ml water. After addition of 350 ml ethyl acetate, agitation is continued for 10 minutes, the inhomogeneous mixture is filtered over a clarification layer, the organic phase is then separated and, after washing once with water, dried over magnesium sulfate. After evaporation of the solvent, the crystalline residue is suspended in diisopropyl ether, and the crystals are filtered off. M.p. 255°–259° C.

(e) The samples of 3-(4-chloro-3-sulfamoylbenzoyl)-2-methylindole obtained according to methods (a) to (d) have identical IR spectra and show mixed melting points without depression.

EXAMPLE 11

3-(4-Chloro-3-methylsulfamoylbenzoyl)-2-methylindole is obtained as described in Example 10 a) from 2.68 g 4-chloro-3-methylsulfamoylbenzoyl chloride and 1.3 g 2-methylindole in the presence of 2.7 g aluminum chloride in dichloroethane. Colorless crystals, m.p. 246° C.

EXAMPLE 12

3-(4-Chloro-3-sulfamoylbenzoyl)-2,5-dimethylindole is obtained as described in Example 10 (a) from 10 g 4-chloro-3-sulfamoylbenzoyl chloride and 7.8 g 2,5-dimethylindole in dichloro-ethane in the presence of 12 g aluminum chloride. M.p. 248°–250° C.

EXAMPLE 13

3-(4-Chloro-3-sulfamoylbenzoyl)-1,2-dimethylindole is obtained as described in Example 10 (a) from 10 g 4-chloro-3-sulfamoylbenzoyl chloride and 6.53 g 1,2-dimethylindole in dichloro-ethane in the presence of 12 g aluminum chloride. After treatment with isopropanol, crystals having a melting point of 247°–249° C. are obtained.

EXAMPLE 14

2-(4-Chloro-3-sulfamoylbenzoyl)-benzo[b]furan

I. (a) 8 g 4-Chloro-3-sulfamoylbenzonitrile and 12 g nickel/aluminum alloy (1:1) are refluxed for 2 hours in 120 ml 75% aqueous formic acid, subsequently filtered off in hot state, and the unreacted metal powder is washed several times with hot methanol. After concentration, water is added, and the crystalline 4-chloro-3-sulfamoylbenzaldehyde (m.p. 162°–164° C.) is filtered off.

(b) 6 g (0.03 mol) 2-bromobenzo[b]furan are dissolved in 20 ml diethyl ether, and added in one portion to a solution of 0.033 mol n-butyl-lithium in 150 ml anhydrous tetrahydrofuran cooled to −70° C. Agitation is continued for about 5 minutes, and a mixture of 2.2 g (0.01 mol) 4-chloro-3-sulfamoylbenzaldehyde in 30 ml anhydrous tetrahydrofuran is added in small portions, while maintaining the reaction mixture at a temperature of −40° to −70° C. Agitation is continued first for 20 minutes at −40° C., and then 30 hours at room temperature and 6 further hours at 50° C., and the mixture is subsequently treated under ice cooling with 10 ml of a saturated ammmonium chloride solution. The precipitate is filtered off, washed several times with ethyl acetate, the united organic phases are dried over magnesium sulfate, and the solvent is evaporated under reduced pressure. Colorless crystals, decomposition point 148° C.

(c) 1.69 g (0.05 mol) 4-Chloro-3-sulfamoylphenyl-2'-benzo[b]furanyl-carbinol are dissolved in 40 ml acetonitrile and stirred for 60 hours after addition of 6 g active manganese dioxide. The inorganic material is filtered off, washed once with acetonitrile, concentrated under reduced pressure, and the residue is recrystallized from a small amount of glacial acetic acid. Colorless crystals, m.p. 170°–172° C.

II. A mixture of 2.16 g 4-chloro-3-sulfamoylbenzonitrile in 50 ml absolute tetrahydrofuran is added to a solution prepared according to I(b) of 2-benzo[b]furyl-lithium in tetrahydrofuran, and the batch is refluxed for 18 hours with thorough agitation and under nitrogen protection. Subsequently, the solvent is distilled off under reduced pressure, icewater is added to the residue, and its pH is made acidic with 2N HCl. Agitation is continued for 2 hours at room temperature, the oil is extraced with 100 ml ethyl acetate, the organic phase is washed twice with water and dried over sodium sulfate, After having distilled off the solvent under reduced pressure, a slightly yellow oil is obtained which is stirred for 20 minutes at room temperature in 20% aqueous KOH, and added dropwise to a thoroughly agitated, saturated, aqueous ammonium chloride solution. The product is suction-filtered and recrystallized from a small amount of glacial acetic acid. Colorless crystals, m.p. 167°–170° C.

III. 4 g 2-Bromo-4'-chloro-3'-sulfamoylacetophenone and 1.63 g salicylaldehyde are maintained for 2 hours with agitation and with exclusion of moisture at a temperature of 80° C. in 50 ml anhydrous dimethyl formamide, in the presence of 2.9 g potassium carbonate ground under anhydrous conditions. After cooling, the batch is poured into a mixture of icewater and excess hydrochloric acid, extracted with ethyl acetate and dried over sodium sulfate. After having distilled off the solvent, crystallization is carried out from di-isopropyl ether and isopropanol. M.p. 152°–156° C. Recrystallization from glacial acetic acid after clarification with active charcoal gives colorless crystals having a melting point of 167°–170° C.

EXAMPLE 15

2-(4-Chloro-3-sulfamoylbenzoyl)-3-methyl-benzo[b]thiophene is obtained as described in Example 1 from 2.5 g 4-chloro-3-sulfamoylbenzoyl chloride, 1.6 g 3-methylbenzo[b]thiophene and 3 g aluminum chloride in 50 ml chlorobenzene. Colorless crystals, m.p. 210° C.

EXAMPLE 16

2-(4-Chloro-3-sulfamoylbenzoyl)-3-methylindole is obtained as described in Example 10 (a) from 10.0 g 4-chloro-3-sulfamoylbenzoyl chloride and 5.1 g 3-methylindole in the presence of 10.4 g aluminum chloride. Colorless crystals from isopropanol, m.p. 205° C.

EXAMPLE 17

3-(4-Chloro-3-sulfamoylbenzoyl)-2-methylbenzo[b]furan (a) 3-(4-Chloro-3-nitrobenzoyl)-2-methylbenzo[b]furan 4.4 g 4-Chloro-3-nitrobenzoyl chloride and 2.6 g 2-methylbenzo[b]furan are dissolved in 50 ml chlorobenzene, cooled to 0° C., and, after addition of 4 g anhydrous aluminum chloride, stirred for 1 hour at 0° to 5° C. After standing overnight at room temperature, the batch is poured into ice-water, extracted several times with ethyl acetate, the united organic phases are washed with water and thoroughly stirred with an aqueous NaHCO₃ solution (pH 8–9), until the small amounts of 4-chloro-3-nitrobenzoyl chloride have disappeared. The batch is dried over sodium sulfate, the solvent is distilled off under reduced pressure, and the residue is crystallized from ether. M.p. 122° C.

(b) 3-(3-Amino-4-chlorobenzoyl)-2-methylbenzo[b]furan is obtained as described in Example 8 (b) from 3.2 g 3-(4-chloro-3-nitrobenzoyl)-2-methylbenzo[b]furan with 9.6 g nickel/aluminum alloy (1:1). M.p. 103° C.

(c) 3-(4-Chloro-3-chlorosulfonylbenzoyl)-2-methylbenzo[b]furan is obtained as described in Example 8 (c) from 3-(3-amino-4-chlorobenzoyl)-2-methylbenzo[b]furan. Colorless crystals m.p. 138° C.

(d) 3-(4-Chloro-3-sulfamoylbenzoyl)-2-methylbenzo[b]furan is obtained by reaction of 2.3 g 3-(4-chloro-3-chlorosulfonylbenzoyl)-2-methylbenzo[b]furan in a mixture of 20 ml methanol and 10 ml anhydrous ammonia. After standing overnight the solvent is distilled off, the residue is absorbed in water and filtered off. Colorless crystals from a small amount of ethanol, m.p. 180°–183° C.

EXAMPLE 18

2-(4-Chloro-3-sulfamoylbenzoyl)-7-methoxybene[b]furan (a) 2-(4-Chloro-3-nitrobenzoyl)-7-methoxybenzo[b]furan 2 g KOH are dissolved in 50 ml methanol, a solution of 5.4 g 2-hydroxy-3-methoxybenzaldehyde is added and subsequently a suspension of 10 g 2-bromo-4'-chloro-3'-nitroacetophenone in 75 ml methanol. The batch is refluxed for 6 hours, agitation is continued overnight at room temperature, and the crystals are suction-filtered. M.p. 136° C. (from ethyl acetate).

(b) 2-(3-Amino-4-chlorobenzoyl)-7-methoxybenzo[b]furan is obtained as described in Example 8b) from 2.2 g 2-(4-chloro-3-nitrobenzoyl)-7-methoxybenzo[b]furan and 6.6 g nickel/aluminum alloy (1:1). Colorless crystals, m.p. 180° C. (from ethanol).

(c) 2-(4-Chloro-3-chlorosulfonylbenzoyl)-7-methoxybenzo[b]furan is obtained as described in Example 8 (c) from 2-(3-amino-4-chlorobenzoyl)-7-methoxybenzo[b]furan. M.p. 143°–145° C.

(d) 2-(4-Chloro-3-sulfamoylbenzoyl)-7-methoxybenzo[b]furan is obtained as described in Example 8 (d) from 2-(4-chloro-3-chlorosulfonylbenzoyl)-7-methoxybenzo[b]furan and 25% aqueous ammonia solution. M.p. 167°–171° C.

EXAMPLE 19

3-(4-Chloro-3-methylsulfamoylbenzoyl)-2-methylbenzo[b]furan is obtained by treating 4.5 g 3-(4-chloro-3-chlorosulfonylbenzoyl)-2-methylbenzo[b]furan with a mixture of 20 ml methanol and 30 ml 40% aqueous methylamine solution for 12 hours at room temperature, by subsequently evaporating the solvent, adding water and filtering the crystals, M.p. 146° C.

EXAMPLE 20

3-(4-Chloro-3-sulfamoylbenzoyl)-2-methylbenzo[b]thiophene is obtained as described in Example 10 (a) from 4-chloro-3-sulfamoylbenzoyl chloride and 2-methylbenzo[b]thiophene in dichloro-ethane in the presence of aluminum chloride.

What is claimed is:

1. A compound of the formula I

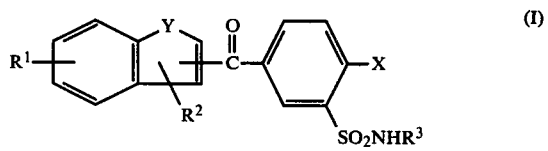

in which R¹ is hydrogen, halogen, alkyl having from 1 to 3 carbon atoms, methoxy or ethoxy; R² and R³, being identical or different, each are hydrogen or alkyl having from 1 to 4 carbon atoms; X is a halogen atom, methyl or trifluoromethyl; and Y is oxygen, sulfur or NR⁴, R⁴ being hydrogen or alkyl having from 1 to 4 carbon atoms.

2. A compound as claimed in claim 1 which is 2-Ethyl-3-(4-chloro-3-sulfamoylbenzoyl)-benzo[b]furan.

3. A compound as claimed in claim 1 which is 3-(4-Chloro-3-sulfamoylbenzoyl)-2-methylbenzo[b]furan.

4. A compound as claimed in claim 1 which is 3-(4-Chloro-3-sulfamoylbenzoyl)-2-methylindole.

5. A compound as claimed in claim 1 which is 3-(4-Chloro-3-methylsulfamoylbenzoyl)-2-methylindole.

6. A compound as claimed in claim 1 which is 2-(4-Chloro-3-sulfamoylbenzoyl)-benzo[b]furan.

7. A compound as claimed in claim 1 which is 2-(4-Chloro-3-sulfamoylbenzoyl)-7-methoxy-benzo[b]furan.

8. A compound as claimed in claim 1 which is 3-(4-Chloro-3-sulfamoylbenzoyl)-2-methylbenzo[b]thiophene.

9. A compound as claimed in claim 1 which is 2-(4-Chloro-3-sulfamoylbenzoyl)-3-methylbenzo[b]thiophene.

10. A pharmaceutical composition having uricosuric, hypouricemic and salidiuretic action containing 5 to 1000 mg per dosage unit of a compound as claimed in claim 1 and a carrier therefor.

11. A method of treatment which comprises administering to a patient a uricosurically, hypouricemically and/or salidiuretically effective amount of a compound as defined in claim 1.